United States Patent
Neumann et al.

(10) Patent No.: US 7,266,472 B2
(45) Date of Patent: Sep. 4, 2007

(54) METHOD FOR DETERMINATING OF AN OIL CONDITION

(75) Inventors: Dieter Neumann, Neukirch (DE); Christian Schwemer, Friedrichshafen (DE); Rainer Grundler, Bodmann (DE); Jens Wagner, Langenargen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 0 days.

(21) Appl. No.: 11/305,412

(22) Filed: Dec. 16, 2005

(65) Prior Publication Data
US 2006/0155502 A1 Jul. 13, 2006

(30) Foreign Application Priority Data
Jan. 13, 2005 (DE) .................... 10 2005 001 547

(51) Int. Cl.
*G01N 33/30* (2006.01)
(52) U.S. Cl. ............... 702/177; 340/457.4; 701/30; 73/53.05
(58) Field of Classification Search ........... 702/30, 702/45–49, 130, 132, 136, 176–178, 22, 702/23, 25, 32, 50, 81; 340/500, 584, 588, 340/450.3, 457.4; 701/30, 31; 73/53.05, 73/53.06, 53.07, 61.76
See application file for complete search history.

(56) References Cited

U.S. PATENT DOCUMENTS

| 4,007,629 | A | | 2/1977 | Hochstein |
| 4,677,847 | A | | 7/1987 | Sawatari et al. |
| 4,970,492 | A | * | 11/1990 | King .................. 340/450.3 |
| 5,777,211 | A | | 7/1998 | Binienda et al. |
| 6,449,538 | B1 | * | 9/2002 | Kubo et al. .................. 701/30 |

FOREIGN PATENT DOCUMENTS

| DE | 26 50 503 | 5/1977 |
| DE | 195 48 260 A1 | 7/1997 |
| EP | 0 231 055 A2 | 8/1987 |
| WO | WO-98/22818 | 5/1998 |

* cited by examiner

*Primary Examiner*—Eliseo Ramos-Feliciano
*Assistant Examiner*—Manuel L Barbee
(74) *Attorney, Agent, or Firm*—Davis Bujold & Daniels, P.L.L.C.

(57) ABSTRACT

A method for determining an oil condition, namely, an oil condition corresponding to the oil age or oil damage, with the following steps: a) measuring a temperature of the oil or of the part through which the oil flows, coordinating each temperature measured with one temperature range defined by an upper limit and/or a lower limit; b) as soon as the measured temperature exceeds or falls below a limit of a temperature range, measuring the period of time during which the measured temperature dwells in this range; c) in addition, integrating an oil flow running during this time over the time period measured in step b); d) from the time period measured in step b) and the integral of the oil flow determined in step c), determining an oil age or oil damage characteristic for the current temperature range.

12 Claims, No Drawings

METHOD FOR DETERMINATING OF AN OIL CONDITION

This application claims priority from German Application Serial No. 10 2005 001 547.6 filed Jan. 13, 2005.

FIELD OF THE INVENTION

A method for determining an oil condition, namely a condition of oil corresponding to oil aging or oil damage.

BACKGROUND OF THE INVENTION

According to the prior art, to minimize the friction between parts moving against each other thus minimizing a wear of the parts, a lubrication between the parts moved relative to each other is established; the oil being preferably used as a lubricant in the lubrication of vehicle transmissions, for example. Vehicle transmissions, the same as other oil lubricated parts, are more and more exposed to increasing loads whereby the oil ultimately used for lubrication is constantly exposed to rising temperatures. If the lube oil is always exposed to high temperatures, the aging, the same as the damage of the lube oil is accelerated. To prevent damage of the lubricated parts due to old lube oil, it is accordingly desirable to detect the age or damage of the oil so as to change the oil in good time according to the age or damage of the oil. From the prior art, no method has so far become known with which the age or damage of lube oil can be reliably determined.

Departing from this, the problem on which this invention is based is to provide a novel method for determining an oil condition, namely, an oil condition corresponding to age or damage of the oil.

SUMMARY OF THE INVENTION

The inventive method comprises at least the following steps:

a) measuring a temperature of the oil or of the part through which the oil flows, coordinating each temperature measured with one temperature range defined by an upper limit and/or a lower limit;

b) as soon as the measured temperature exceeds or falls below a limit of a temperature range, measuring the period of time during which the measured temperature dwells in this range;

c) in addition integrating an oil fow running during this time over the time period measured in step b);

d) from the time period measured in step b) and the integral of the oil flow determined in step c), determining an oil age or oil damage characteristic for the current temperature range.

DETAILED DESCRIPTION OF THE INVENTION

The instant invention proposes a fully automatically developing method for determining a condition of lube oil corresponding to age or damage. It is possible with the aid of the inventive method to automatically and at the right time start an oil change so as to prevent damage of the parts to be lubricated.

The integral of the oil flow determined in step d) is preferably multiplied by the time period measured in step c) and divided by the total oil volume, a value here determined being added to a value optionally determined previously in the same manner for the same temperature range, a characteristic accumulated oil age or oil damage value being thus determined for the actual temperature range.

According to an advantageous development of the invention, for each temperature range is separately checked whether the determined, accumulated oil age or oil damage value exceeds a preset limit value, and if a limit value of a temperature range has been exceeded, an oil change signal is produced.

According to an alternative advantageous development of the invention from the accumulated oil age or oil damage value of the individual temperature ranges, a mean oil age or oil damage value preferably comprising all temperature ranges is determined checking whether said averaged oil age or oil damage value exceeds a preset limit value and then, if this limit value has been exceeded, an oil change signal is produced.

Preferred teaching of the current invention stem from the dependent claims and the following description. A described embodiment of the invention should not be limited by the following description.

The detailed description of the inventive method that follows starts from the fact that with the inventive method a condition of the transmission oil is determined corresponding to oil age or oil damage. The oil serves to lubricate a vehicle transmission. During operation, the load of the vehicle transmission and therewith the temperature to which the transmission oil is exposed, changes. In accordance with the invention, the operating temperature range of the vehicle transmission is subdivided into temperature ranges. Each one of the temperature ranges is preferably defined by a lower limit and an upper limit, wherein the temperature range, comprising the lowest temperatures, also can have only one upper limit and the temperature range, comprising the highest temperatures, can also have only one lower limit. The exact number N of temperature ranges and the fixing of the temperature limits for the temperature ranges being incumbent upon the expert concerned here.

According to the instant invention, the temperature of the oil or of the vehicle transmission or the part through which the transmission oil flows is now measured. During the operation of the vehicle transmission, each measured temperature is coordinated with one temperature range. When measuring the temperature, if it has been determined that the measured temperature exceeds or falls below a temperature limit of one range and, consequently, a new temperature range appears, a time meter is started and the time period during which the measured temperature dwells in the new temperature range is measured. Then, when the measured temperature leaves said range, the time meter is stopped, namely, reset.

Furthermore, according to the instant invention, an oil flow running during this time is integrated over the above measured or determined time period. If the measured temperature consequently appears in a new temperature range, then, on one hand, the period of swell of the temperature in this range is measured and, on the other hand, over said period of dwell, the oil flow running during this time is integrated.

In addition to this, the determined duration of swell of the oil in the temperature range, the same as the integral of the determined oil flow over this time period, are multiplied by each other and divided by the total volume of oil in the vehicle transmission. The determined value thus corresponds to an age of the oil during the period of dwell thereof in one temperature range. This value is added to a optional value previously determined in the same manner for the same temperature range in order thus to determine for the current temperature range a characteristic accumulated oil age or oil damage value.

The characteristic accumulated oil age or oil damage value is, therefore, determined for a temperature range according to the following equation:

$$\text{sum } [i] = \text{sum}_{alt}[i] + \frac{\int \dot{V}[i] * dt}{V_{ges}} * T[i]$$

wherein:
$\dot{V}$ [i]=oil flow in the temperature range i,
$V_{ges}$=total volume of oil,
T[i]=time period for which the temperature dwells in the temperature range i,
sum[i]=accumulated, characteristic oil age or oil damage value to bet determined for the temperature range i,
$\text{sum}_{alt}$[i]=previously determined characteristic oil age or oil damage value for the temperature range i.

It is, therefore, in conformity with the instant invention to measure the temperature of the oil of the transmission or of the vehicle transmission or part of the vehicle transmission through which the oil flows, to coordinate the temperature with a one time range and to determine the time for which the measured temperature dwells in this time period. In addition, the oil flow through the vehicle transmission or part of the vehicle transmission is mathematically integrated over the period of dwell and from these values thus determined oil age characteristic is determined for the temperature range. This calculation process is started anew whenever the measured temperature appears in a new range.

According to the instant invention, it is now possible to check for each temperature range whether the characteristic accumulated oil value for the temperature range determined by using the above formula exceeds a preset limit value for the current temperature range. If this limit value has been exceeded, in accordance with the instant invention, it automatically initiates a change of the transmission oil so that an oil change signal is produced or generated. To produce the oil change signal, it suffices here that the preset value be exceeded for only one temperature range. The limit values of the individual temperature ranges preferably differ from each other so as thus to take into account the accelerated aging of the oil occurring at high temperatures.

Alternatively, it is possible to calculate with each other the characteristic and accumulated oil aging values determined by using the above formula so that from them there is determined one oil age value averaged over all temperature ranges. If it is concluded here that the averaged oil age value exceeds a preset limit value, an oil change signal can again be generated. When determining a mean oil value, it is preferred to evaluate the oil age values of the individual temperature ranges with different strictness. The oil age values of the temperature ranges which cover the critical temperature ranges are thus preferably more strictly evaluated than the oil age values of the temperature ranges which cover moderate operating temperatures. In this manner, it is possible to take into account the circumstance that at extreme operating temperatures, the oil ages more quickly than at moderate temperatures.

The invention claimed is:

1. A method for determining a condition of lubricating oil corresponding to an oil age or an oil damage value of the oil, the method comprising the steps of:

measuring a temperature of one or more of the oil and a part through which the oil flows and coordinating each measured temperature with a temperature range defined by at least one of an upper limit and a lower limit;

measuring, as soon as the measured temperature exceeds or falls below a limit of the temperature range, a first period of time during which the measured temperature dwells in the temperature range which exceeds the upper limit or falls below the lower limit;

integrating a flow of oil running during the time period over the first period;

determining the oil age or the oil damage value representing at least one of the oil age and oil damage for a current temperature range from the first period time and the integral of the flow of oil; and providing an output representing the condition of the oil based upon the determined oil age or the oil damage value; and producing an oil change signal when the oil age or the oil damage valued exceeds a preset limit value is exceeded indicating that an oil change is required.

2. The method according to claim 1, further comprising the step of starting a time meter when the measured temperature one of exceeds or falls below the temperature limit, and measuring the time period during which the measured temperature dwells in the temperature range, and resetting the time meter when the measured temperature falls outside the temperature range.

3. The method according to claim 1, further comprising the step of determining a current oil age or a current oil damage value by multiplying an integral of the oil flow by the time period and divided dividing by a total oil volume of the oil.

4. The method according to claim 3, further comprising the step of determining the oil age or the oil damage value representing an accumulated oil age or accumulated oil damage value for the current temperature range by adding the current oil age or the current oil damage value to a previously determined oil age or a previously determined oil damage value determined by multiplying an integral of a previous oil flow by a previous time period divided by the total oil volume value optionally previously determined in the same manner for the same temperature range and thus a characteristic accumulated oil age or oil damage value is determined for the current temperature range.

5. The method according to claim 4, further comprising the step of checking each temperature range to determine whether the oil age or the oil damage value exceeds a preset limit value for the current temperature range.

6. The method according to claim 4, further comprising the step of determining a mean oil age value or a mean oil damage value from at least one of the oil age and or the oil damage value of an individual temperature range, which preferably comprises all temperature ranges, and checking whether an averaged oil aging or averaged oil damage value exceeds a preset limit value.

7. The method according to claim 6, further comprising the step of in evaluating at least one of the mean oil age or the mean oil damage value for the individual temperature ranges with different strictness.

8. The method according to claim 1, further comprising the step of calculating at least one of the oil age value and the oil damage value of the individual temperature ranges from the following equation:

$$\text{sum}[i] = \text{sum}_{alt}[i] + \frac{\int \dot{V}[i] * dt}{V_{ges}} * T[i]$$

where:
$\dot{V}[i]$=oil flow in the temperature range I,
$V_{ges}$=total volume of oil,
T[i]=time period for which the temperature dwells in the temperature range I,
sum[i]=accumulated, characteristic oil aging or oil damage value to be determined for the temperature range I, and
$\text{sum}_{alt}[i]$=previously determined characteristic oil aging or oil damage value for the temperature range I.

9. A method for determining a condition of lubricating oil, flowing within a transmission, corresponding to an oil age or an oil damage value of the oil, the method comprising the steps of:
measuring a temperature of at least one of the oil and a part through which the oil flows and coordinating each measured temperature with a temperature range defined by at least one of an upper limit and a lower limit;
measuring, as soon as the measured temperature exceeds the upper limit of the temperature range or falls below the lower limit of the temperature range, a period of time during which the measured temperature exceeds the upper limit of the temperature range or falls below the lower limit of the temperature range;
integrating a flow of oil flowing during the period of time;
determining, from the period of time and the integral of the flow of oil, at least one of the oil age and the oil damage for a current temperature range;
providing an output representing the condition of the oil based upon the determined oil age or the oil damage value; and
when the oil age or the oil damage valued exceeds a preset limit value, generating an oil change signal indicating a need for changing the oil of the transmission.

10. The method according to claim 9, further comprising the step of calculating at least one of the oil age value and the oil damage value of the individual temperature ranges from the following equation:

$$\text{sum}[i] = \text{sum}_{alt}[i] + \frac{\int \dot{V}[i] * dt}{V_{ges}} * T[i]$$

where:
$\dot{V}[i]$=oil flow in the temperature range I,
$V_{ges}$=total volume of oil,
T[i]=time period for which the temperature dwells in the temperature range I,
sum[i]=accumulated, characteristic oil aging or oil damage value to be determined for the temperature range I, and
$\text{sum}_{alt}[i]$=previously determined oil aging or oil damage value characteristic for the temperature range I.

11. A method for determining a condition of lubricating oil, flowing within a transmission, corresponding to an oil age or an oil damage value of the oil, the method comprising the steps of:
a) measuring a temperature of at least one of the oil and a part through which the oil flows and coordinating each measured temperature with a temperature range defined by at least one of an upper limit and a lower limit;
b) measuring a period of time during which the measured temperature exceeds the upper limit or falls below the lower limit by starting a time meter, as soon as the measured temperature exceeds the upper limit of the temperature range or the lower limit of the temperature range, and stopping the time meter as soon as the measured temperature falls within the temperature range, and resetting the time meter;
c) integrating a flow of oil flowing during the period of time;
d) determining, from the period of time end the integral of the flow of oil, at least one of the oil age and the oil damage for a current temperature range;
e) providing an output representing the condition of the oil based upon the determined oil age or the oil damage value;
f) repeating steps b through e each time the measured temperature exceeds the upper limit or falls below the lower limit; and
when the output, representing the condition of the oil based upon the determined oil age or the oil damage value, exceeds a preset limit value, generating an oil change signal indicating a need for changing the oil of the transmission.

12. The method according to claim 11, further comprising the step of calculating at least one of the oil age value and the oil damage value of the individual temperature ranges from the following equation:

$$\text{sum}[i] = \text{sum}_{alt}[i] + \frac{\int \dot{V}[i] * dt}{V_{ges}} * T[i]$$

where:
$\dot{V}[i]$=oil flow in the temperature range I,
$V_{ges}$=total volume of oil,
T[i]=time period for which the temperature dwells in the temperature range I,
sum[i]=accumulated, characteristic oil aging or oil damage value to be determined for the temperature range I, and
$\text{sum}_{alt}[i]$=previously determined oil aging or oil damage value characteristic for the temperature range I.

* * * * *